US011410341B2

(12) United States Patent
Baenen et al.

(10) Patent No.: US 11,410,341 B2
(45) Date of Patent: Aug. 9, 2022

(54) SYSTEM AND METHOD FOR VISUALIZING PLACEMENT OF A MEDICAL TUBE OR LINE

(71) Applicant: GE PRECISION HEALTHCARE LLC, Wauwatosa, WI (US)

(72) Inventors: Alec Joseph Baenen, Hartland, WI (US); Pal Tegzes, Budapest (HU); Levente Torok, Budapest (HU); Teri Lynn Fischer, Germantown, WI (US); Katelyn Rose Nye, Glendale, WI (US); Gireesha Chinthamani Rao, Pewaukee, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/953,517

(22) Filed: Nov. 20, 2020

(65) Prior Publication Data
US 2022/0164996 A1 May 26, 2022

(51) Int. Cl.
G06T 11/00 (2006.01)
G06T 7/00 (2017.01)
G06T 7/73 (2017.01)
G16H 20/40 (2018.01)
G16H 30/40 (2018.01)

(52) U.S. Cl.
CPC ............ G06T 11/00 (2013.01); G06T 7/0014 (2013.01); G06T 7/74 (2017.01); G16H 20/40 (2018.01); G16H 30/40 (2018.01); G06T 2207/20081 (2013.01); G06T 2207/20084 (2013.01); G06T 2207/30021 (2013.01)

(58) Field of Classification Search
None
See application file for complete search history.

(56) References Cited

U.S. PATENT DOCUMENTS

2009/0297441 A1*  12/2009  Canham .................. A61K 49/06
                                                        424/9.4
2017/0215762 A1*   8/2017  Burnside ................ A61B 5/066
2020/0211694 A1    7/2020  Nye et al.

OTHER PUBLICATIONS

Yi, Xin, et al.; "Automatic Catheter Detection in Pediatric X-Ray Images Using a Scale-Recurrent Network and Synthetic"; 1st Conference on Medical Imaging with Deep Learning (MIDL, 2018); 10 pages.

Frid-Adard, Maayan, et al.; "Endotracheal Tube Detection and Segmentation in Chest Radiographs Using Synthetic Data", RADLogics Ltd., Department of Biomedical Engineering, Tel Aviv University, 2019; 9 pages.

(Continued)

Primary Examiner — Yanna Wu
(74) Attorney, Agent, or Firm — Fletcher Yoder, P.C.

(57) ABSTRACT

An image processing system is provided. The image processing system includes a display, a processor, and a memory. The memory stores processor-executable code that when executed by the processor causes receiving an image of a region of interest of a patient with a medical tube or line disposed within the region of interest, detecting the medical tube or line within the image, generating a combined image by superimposing a first graphical marker on the image that indicates an end of the medical tube or line, and displaying the combined image on the display.

16 Claims, 13 Drawing Sheets

(56) References Cited

OTHER PUBLICATIONS

Huo, Zhimin et al.; "Computer-aided detection of malpositioned endotracheal tubes in portable chest radiographs", Progress in Biomedical Optics and Imaging, SPIE, vol. 9035, Mar. 2014; pp. 1-6.
Lakhani, Paras; "Deep Convolutional Neural Networks for Endotracheal Tube Position and X-ray Image Classification: Challenges and Opportunities", Journal of Digital Imaging, vol. 30, No. 4, Jun. 2017; pp. 460-468.
Yi, Xin, et al.; "Computer-Aided Assessment of Catheters and Tubes on Radiographs: How Godo is Artificial Intelligence for Assessment?", Cornell University Ithaca, NY, Feb. 2020; pp. 1-12.
Extended EP Search Report; Application No. 21207544.4-1210; dated Apr. 2022; pp. 1-11.

* cited by examiner

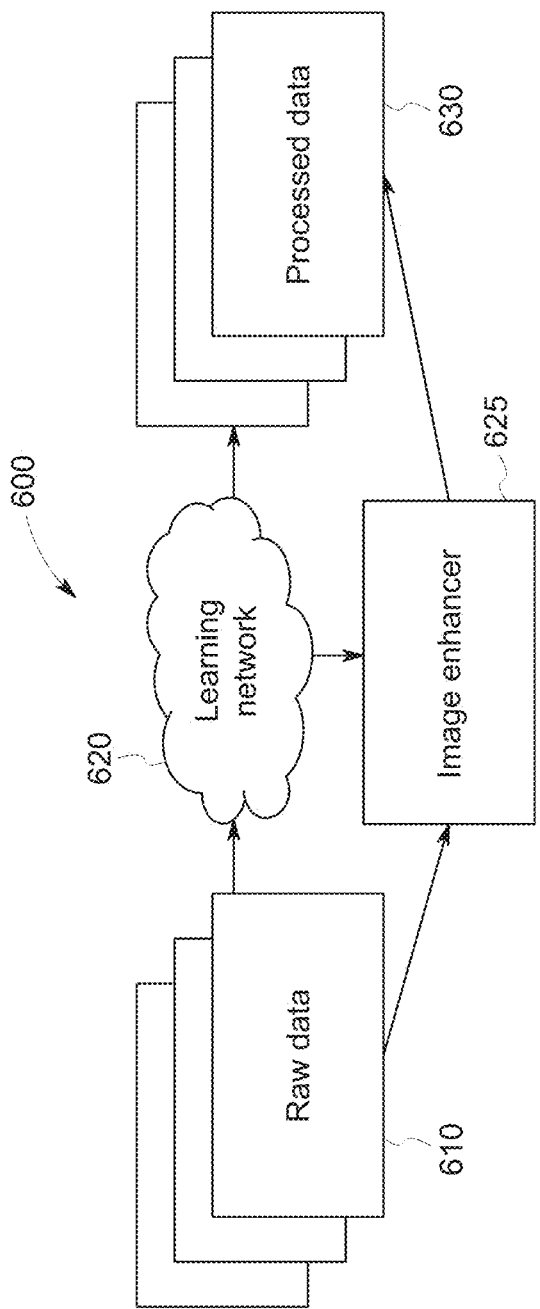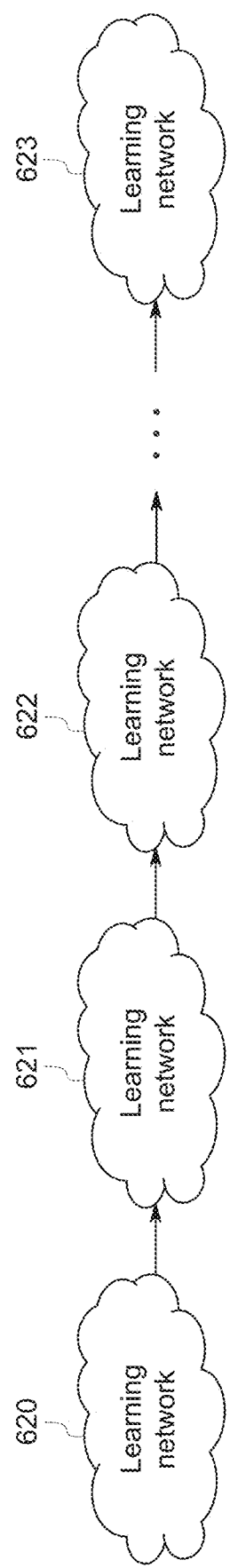
FIG. 6A
FIG. 6B

SYSTEM AND METHOD FOR VISUALIZING PLACEMENT OF A MEDICAL TUBE OR LINE

TECHNICAL FIELD

The subject matter disclosed herein relates to medical image processing, and more particularly to systems and methods for visualizing placement of a medical tube or line.

BACKGROUND

Medical imaging may be utilized to visualize medically placed tubes or lines (e.g., chest tube, a nasogastric tube, endotracheal tube, vascular line, a peripherally inserted central catheter (PICC), a catheter, etc.). However, it may be difficult for medical personnel (e.g., doctor, radiologist, technician, etc.) to visualize these medically placed tubes or lines. In addition, the medical personnel may be untrained or inexperienced, which may hinder their ability to identify the medically placed tube or line and to determine if it is properly placed. Further, medical personnel may have to manually make measurements (which may be time consuming) to determine if a medically placed tube or line is properly placed. However, if a medically placed tube or line is misplaced, fast intervention is needed to move the tube or line to the appropriate location for patient safety.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In accordance with an embodiment, an image processing system is provided. The image processing system includes a display, a processor, and a memory. The memory stores processor-executable code that when executed by the processor causes receiving an image of a region of interest of a patient with a medical tube or line disposed within the region of interest, detecting the medical tube or line within the image, generating a combined image by superimposing a first graphical marker on the image that indicates an end of the medical tube or line, and displaying the combined image on the display.

In accordance with another embodiment, a method for medical image processing is provided. The method includes receiving, via a processor, an image of a region of interest of a patient with a medical tube or line disposed within the region of interest, detecting, via the processor, the medical tube or line within the image, generating, via the processor, a combined image by superimposing a first graphical marker on the image that indicates an end of the medical tube or line, and causing, via the processor, display of the combined image on a display.

In accordance with a further embodiment, a non-transitory, computer-readable medium is provided. The computer-readable medium includes processor-executable code configured to receive an image of a region of interest of a patient with a medical tube or line disposed within the region of interest, detect the medical tube or line within the image and a reference landmark within the region of interest within the image, generate a combined image by superimposing a first graphical marker on the image that indicates an end of the medical tube or line and a second graphical marker on the image that indicates the reference landmark, and display the combined image on a display.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 6A is a schematic diagram of an embodiment of a configuration to apply a learning network to process and/or otherwise evaluate an image;

FIG. 6B is a schematic diagram of an embodiment of a combination of a plurality of learning networks;

DETAILED DESCRIPTION

Figure 1:
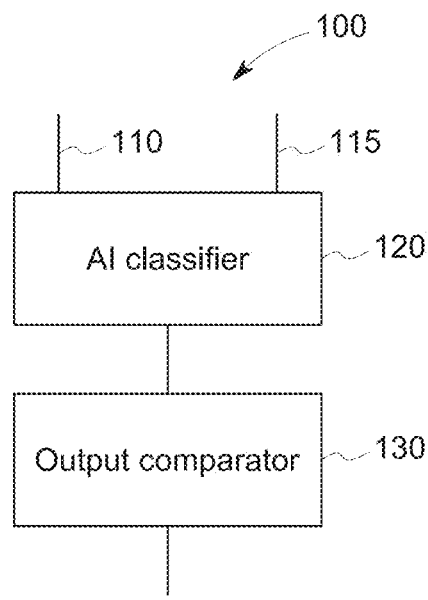
FIG. 1 is a schematic diagram of an embodiment of a condition comparator.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Imaging devices (e.g., gamma camera, positron emission tomography (PET) scanner, computed tomography (CT) scanner, X-Ray machine, fluoroscopy machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, quality control, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine and/or deep learning can be used to help configure, monitor, and update the medical imaging workflow and devices.

Certain examples provide and/or facilitate improved imaging devices which improve diagnostic accuracy and/or coverage. Certain examples facilitate improved image reconstruction and further processing to provide improved diagnostic accuracy.

Certain examples provide an image processing apparatus including an artificial intelligence classifier. The classifier can detect, segment, and quantify pathology, for example. The classifier can be a discrete output of positive or negative for a finding, a segmentation, etc. For example, the classifier can instantiate machine learning and/or other artificial intelligence to detect, segment, and analyze a presence of a medical device (e.g., medically placed tube or line). For example, the classifier can instantiate machine learning and/or other artificial intelligence to detect an end of a medically placed tube or line, detect a reference or anatomical landmark, determine a position of the medically placed tube or line relative to the reference or anatomical landmark, measure a distance between the end of the medically placed tube or line and the reference landmark, and determine whether the tube or line is properly placed.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Certain examples use neural networks and/or other machine learning to implement a new workflow for image and associated patient analysis including generating alerts based on radiological findings that may be generated and delivered at the point of care of a radiology exam. Certain examples use Artificial Intelligence (AI) algorithms to process one or more imaging exams (e.g., an image or set of images), and provide an alert based on the automated exam analysis. The alert(s) (e.g., including notification(s), recommendation(s), other action(s), etc.) may be intended for the technologist acquiring the exam, clinical team providers (e.g., nurse, doctor, etc.), radiologist, administration, operations, and/or even the patient. The alerts may be to indicate a specific or multiple quality control and/or radiological finding(s) or lack thereof in the exam image data, for example.

In certain examples, the AI algorithm can be (1) embedded within an imaging device, (2) running on a mobile device (e.g., a tablet, smart phone, laptop, other handheld or mobile computing device, etc.), and/or (3) running in a cloud (e.g., on premise or off premise) and delivers the alert via a web browser (e.g., which may appear on the radiology system, mobile device, computer, etc.). Such configurations can be vendor neutral and compatible with legacy imaging systems. For example, if the AI processor is running on a mobile device and/or in the "cloud", the configuration can receive the images (A) from the x-ray and/or other imaging system directly (e.g., set up as secondary push destination such as a Digital Imaging and Communications in Medicine (DICOM) node, etc.), (B) by tapping into a Picture Archiving and Communication System (PACS) destination for redundant image access, (C) by retrieving image data via a sniffer methodology (e.g., to pull a DICOM image off the system once it is generated), etc.

Certain examples provide apparatus, systems, methods, etc., to determine progression of a disease and/or other condition based on output of an algorithm instantiated using and/or driven by an artificial intelligence (AI) model, such as a deep learning network model, machine learning network model, etc. For example, the presence of a medically placed tube or line (e.g. chest tube, a nasogastric tube, endotracheal tube, vascular line, a peripherally inserted central catheter, a catheter, etc.) can be determined based on an output of an AI detection algorithm. In addition, the placement of a medical tube or line within a region of interest (e.g., lung, stomach, vascular system, etc.) can be determined based on an output of an AI detection (e.g., whether the medical tube or line is properly placed).

Thus, certain examples provide systems and method to detect a medically placed tube or line within a region of interest of a patient and whether the tube or line is properly placed within the region of interest based on an AI classification algorithm applied to a patient's data. An example method includes detecting a presence of a medically placed tube or line in an image; detecting an end of the medically placed tube or line in the image; detecting a reference or anatomical landmark in the image; determining whether the end of the medically placed tube or line is properly placed relative to the reference or anatomical landmark; and/or providing a notification for a caregiver as to whether the medically placed tube or line is properly placed relative to the reference or anatomical landmark. In certain embodiments, the AI classification algorithm may detect the presence of the medically placed line or tube; graphically mark the medically placed line or tube with a color graphical overlay; detect an end (e.g., distal end) of the medically placed line or tube; graphically mark the end of the medically placed tube or line; detect a reference or anatomical landmark (e.g., for determining the proper placement of the tube or line relative to the landmark); graphically mark the reference or anatomical landmark; calculate a distance between the end of the medically placed tube or line; and/or calculate and provide a confidence metric (e.g., for the calculated distance, for the determination of the presence of the medically placed tube or line, for an accuracy in detecting the end of the tube or line, for an accuracy in detecting the reference or anatomical landmark, etc.). The AI classification algorithm is trained based on images with or without medically placed tubes or lines, images with properly placed tubes or lines, images with misplaced tubes or lines, images with the reference or anatomical landmark, and/or images without the reference or anatomical landmark.

For example, patients in a critical care setting receive chest x-rays (or other regions) to monitor the placement of a medically placed tube or line. If a tube or line is misplaced, the medical team may need to conduct a faster intervention properly placed the medical tube or line. An artificial intelligence classifier can detect a presence of the medically placed tube or line, detect an end of the medically placed tube or line, detect a reference or anatomical landmark, and evaluate whether the tube or line is properly placed. An alert can be generated and output at a point of care, on a device (e.g., an imaging device, an imaging workstation, etc.) to notify and/or otherwise provide instructions (e.g., notification that a tube is or is not properly placed or instruction to remove the tube or line, shift tube or line in a certain direction, etc.) to a clinical care team, for example.

The techniques describe herein provide a quicker means to determine if a medically placed tube or line is improperly placed. This enables a faster intervention to ensure the tube or line is in an appropriate location for patient safety. In addition, it relieves some of the burden on the medical team providing assistance to the patient (especially those personnel who may be untrained or inexperienced).

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, classified and further annotated for object localization, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

FIG. 1 illustrates an example condition comparator apparatus 100 including a plurality of input 110, 115, an artificial intelligence (AI) classifier 120, and an output comparator 130. Each input 110, 115 is provided to the AI classifier 120, which classifies image and/or other information in the respective input 110, 115 to identify a condition in the input 110, 115 and to generate an indication of the identified condition based on the input 110, 115. In certain embodiments, the AI classifier 120 may classify images and/or other information in the respective input 110, 115 to identify a medically placed tube or line (e.g., chest tube, a nasogastric tube, endotracheal tube, vascular line, a peripherally inserted central catheter, a catheter, etc.) and to identify a reference or anatomical landmark relevant to the type or line and its desired placement. Using the example comparator apparatus 100, it can be determined whether an end of the tube or line is properly placed within a region of interest of the patient relative to a reference or anatomical landmark. In particular, both an end of the tube or line and a reference or anatomical landmark may be located and a determination made as to whether the end of the tube or line is properly placed relative to the reference or anatomical landmark. A distance may be measured between the end of the tube or line and the reference or anatomical landmark in determining whether the end of the tube or line is properly placed. A confidence metric (e.g., for the calculated distance, for the determination of the presence of the medically placed tube or line, for an accuracy in detecting the end of the tube or line, for an accuracy in detecting the reference or anatomical landmark, etc.) may be calculated and/or provided via user-perceptible notification or stored for further reference. Further, a notification or alert may be provided as to whether or not the medically placed tube or line is properly placed. If the tube or line is not properly placed, further instructions may be provided via a notification or alert (e.g., related to moving the tube or line in a certain direction).

Figure 2:
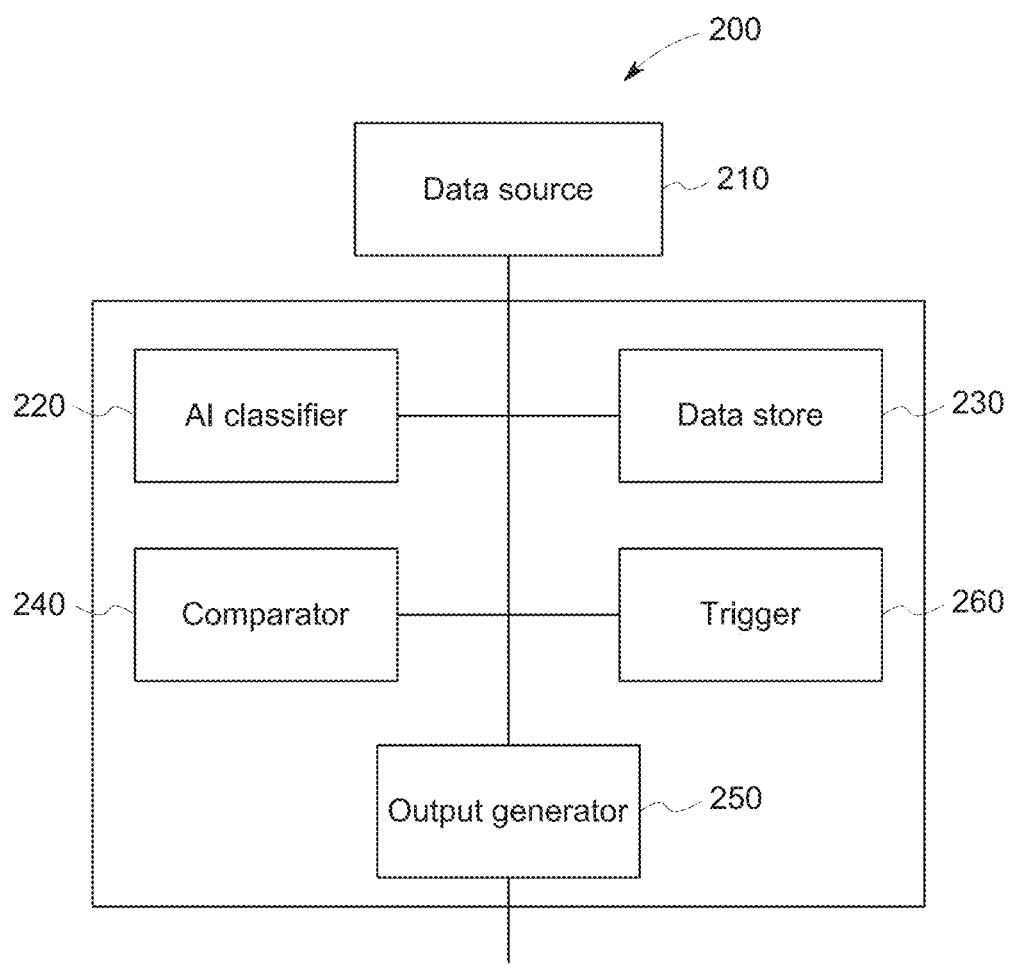
FIG. 2 is a schematic diagram of an embodiment of a clinical progression analysis apparatus.

FIG. 2 illustrates an example clinical progression analysis apparatus 200 that can be constructed based on the example condition comparator 100 of FIG. 1. The example apparatus 200 includes a data source 210, an artificial intelligence (AI) classifier 220, a data store 230, a comparator 240, an output generator 250, and a trigger 260. Input 110, 115 can be provided by the data source 210 (e.g., a storage device, an imaging device, etc., incorporated in and/or otherwise connected to the apparatus 200, etc.) to the AI classifier 220.

The example classifier 220 processes input over time to correlate input from the data source 210 with a classification. Thus, the AI classifier 220 processes input image data and/or other data to identify a condition in the input data and classify that condition according to one or more states (e.g., tube or line present, tube or line not present, reference or anatomical landmark present, reference or anatomical landmark not present, tube or line placed correctly, tube or line misplaced) as specified by an equation, a threshold, and/or other criterion. In certain embodiments, the AI classifier 220 processes input image data and/or other data to detect a medically placed tube or line and to determine whether an end of the medically placed tube or line is properly placed. Output of the AI classifier 220 can be stored in the data store 230, for example.

Over time, classifications made by the AI classifier 220 with respect to the same type of input 110, 115 from the data source 210 (e.g., lung MR images of the same patient taken at times t0 and t1, etc.) can be generated and stored in the data store 230. The classifications are provided to the comparator 240, which compares a classification at two or more different times at two or more different times (e.g., prior to insertion of the tube or line and after the insertion of the tube or line) to identify the medically placed tube or line and determine whether the end of the medically placed tube or line is properly placed. For example, at time t0 the tube or line may not present in the region of interest and at time t1 or a later time end of the tube or line may be placed in a location (which may or may not be properly placed) within the region of interest.

The comparator 240 provides a result indicative of the trend/progression. In certain embodiments, the comparator 240 provides a result indicative of a placement of an end of a medically placed tube or line. The output generator 250 transforms that result into an output that can be displayed, stored, provided to another system for further processing such as an alert, an order, an adjustment in patient care, (e.g., a point of care alert system, an imaging/radiology workstation, a computer-aided diagnosis (CAD) processor, a scheduling system, a medical device, etc.), etc.

The trigger 260 coordinates actions among the data source 210, the AI classifier 220, the data store 230, the comparator 240, and the output generator 250. The trigger 260 can initiate input of data from the data source 210 to the classifier 220, comparison of results from the data store 230 by the comparator 240, output by the output generator 250. Thus, the trigger 260 serves as a coordinator among elements of the apparatus 200.

Figure 3:
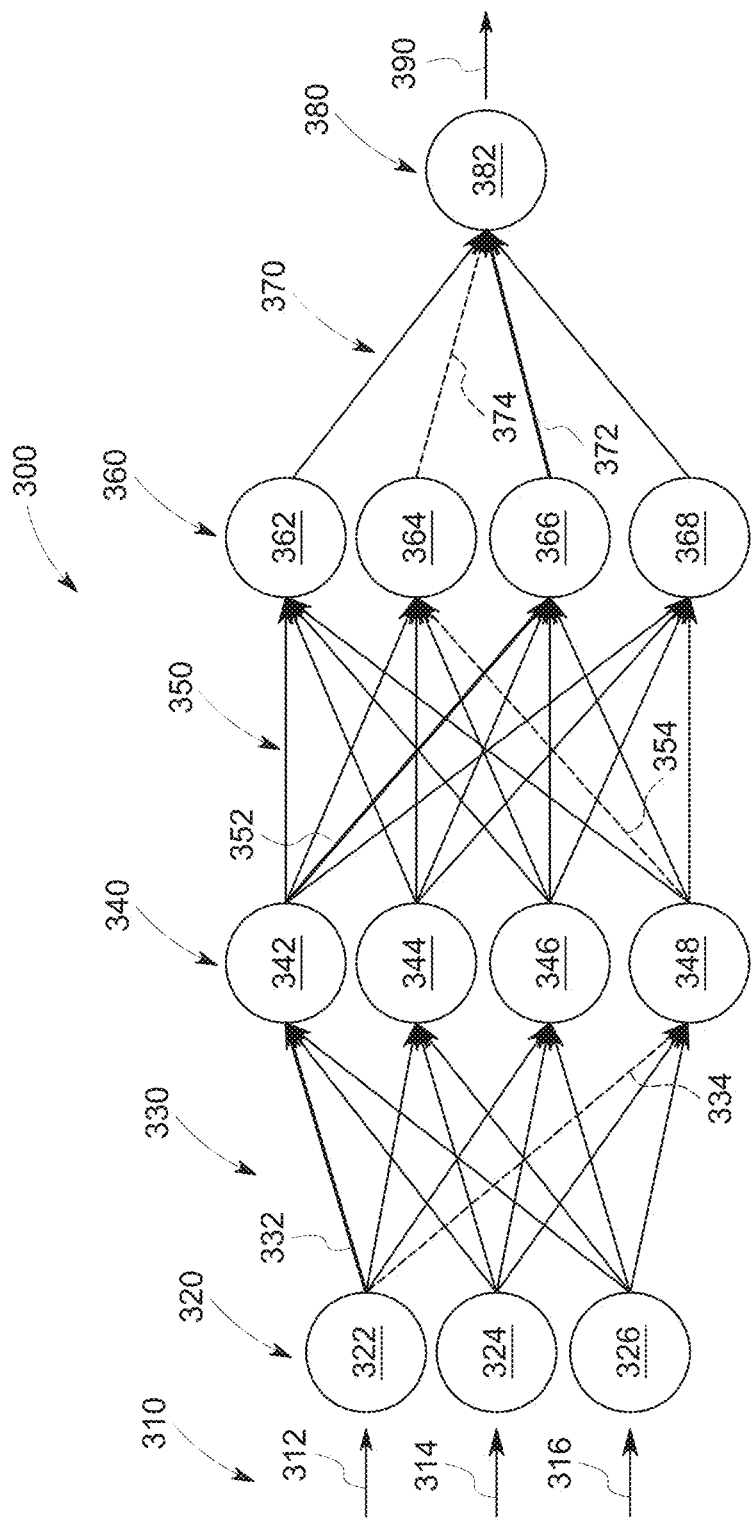
FIG. 3 is a schematic diagram of an embodiment of a learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
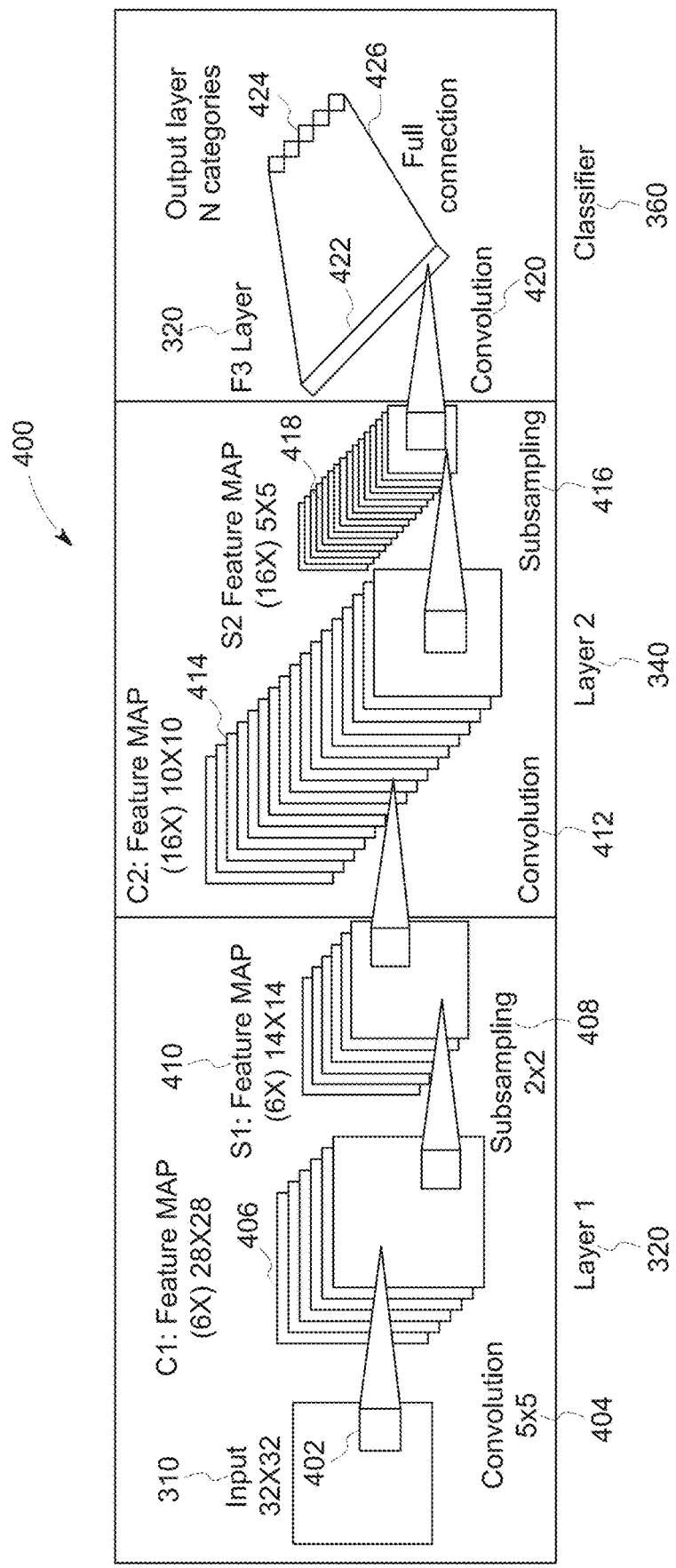
FIG. 4 is a schematic diagram of an embodiment of a particular implementation of the neural network in FIG. 3 as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer e80. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc.). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example.

Figure 5:
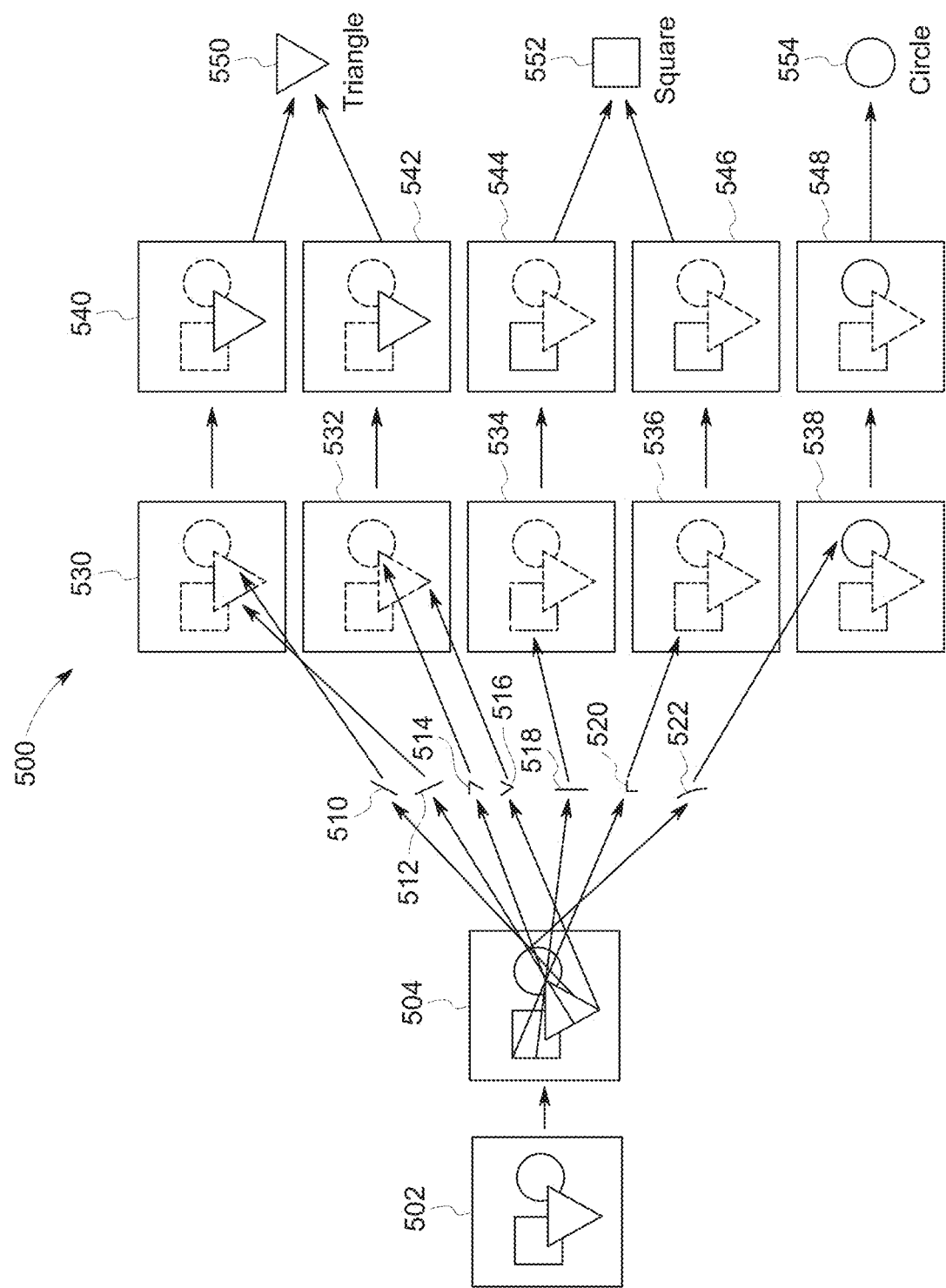
FIG. 5 is a schematic diagram of an embodiment of an image analysis convolutional neural network.

FIG. 5 is a representation of an example implementation of an image analysis convolutional neural network 500. The convolutional neural network 500 receives an input image 502 and abstracts the image in a convolution layer 504 to identify learned features 510-522. In a second convolution layer 530, the image is transformed into a plurality of images 530-538 in which the learned features 510-522 are each accentuated in a respective sub-image 530-538. The images 530-538 are further processed to focus on the features of interest 510-522 in images 540-548. The resulting images 540-548 are then processed through a pooling layer which reduces the size of the images 540-548 to isolate portions 550-554 of the images 540-548 including the features of interest 510-522. Outputs 550-554 of the convolutional neural network 500 receive values from the last non-output layer and classify the image based on the data received from the last non-output layer. In certain examples, the convolutional neural network 500 may contain many different variations of convolution layers, pooling layers, learned features, and outputs, etc.

FIG. 6A illustrates an example configuration 600 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 600 of FIG. 6A, raw data 610 (e.g., raw data 610 such as sonogram raw data, etc., obtained from an imaging scanner such as an x-ray, computed tomography, ultrasound, magnetic resonance, etc., scanner) is fed into a learning network 620. The learning network 620 processes the data 610 to correlate and/or otherwise combine the raw data 620 into processed data 630 (e.g., a resulting image, etc.) (e.g., a "good quality" image and/or other image providing sufficient quality for diagnosis, etc.). The learning network 620 includes nodes and connections (e.g., pathways) to associate raw data 610 with the processed data 630. The learning network 620 can be a training network that learns the connections and processes feedback to establish connections and identify patterns, for example. The learning network 620 can be a deployed network that is generated from a training network and leverages the connections and patterns established in the training network to take the input raw data 610 and generate the resulting image 630, for example.

Once the learning 620 is trained and produces good images 630 from the raw image data 610, the network 620 can continue the "self-learning" process and refine its performance as it operates. For example, there is "redundancy" in the input data (raw data) 610 and redundancy in the network 620, and the redundancy can be exploited.

If weights assigned to nodes in the learning network 620 are examined, there are likely many connections and nodes with very low weights. The low weights indicate that these connections and nodes contribute little to the overall performance of the learning network 620. Thus, these connections and nodes are redundant. Such redundancy can be evaluated to reduce redundancy in the inputs (raw data) 610. Reducing input 610 redundancy can result in savings in scanner hardware, reduced demands on components, and also reduced exposure dose to the patient, for example.

In deployment, the configuration 600 forms a package 600 including an input definition 610, a trained network 620, and an output definition 630. The package 600 can be deployed and installed with respect to another system, such as an imaging system, analysis engine, etc. An image enhancer 625 can leverage and/or otherwise work with the learning network 620 to process the raw data 610 and provide a result (e.g., processed image data and/or other processed data 630, etc.). The pathways and connections between nodes of the trained learning network 620 enable the image enhancer 625 to process the raw data 610 to form the image and/or other processed data result 630, for example.

As shown in the example of FIG. 6B, the learning network 620 can be chained and/or otherwise combined with a plurality of learning networks 621-623 to form a larger learning network. The combination of networks 620-623 can be used to further refine responses to inputs and/or allocate networks 620-623 to various aspects of a system, for example.

In some examples, in operation, "weak" connections and nodes can initially be set to zero. The learning network 620 then processes its nodes in a retaining process. In certain examples, the nodes and connections that were set to zero are not allowed to change during the retraining. Given the redundancy present in the network 620, it is highly likely that equally good images will be generated. As illustrated in FIG. 6B, after retraining, the learning network 620 becomes DLN 621. The learning network 621 is also examined to identify weak connections and nodes and set them to zero. This further retrained network is learning network 622. The example learning network 622 includes the "zeros" in learning network 621 and the new set of nodes and connections. The learning network 622 continues to repeat the processing until a good image quality is reached at a learning network 623, which is referred to as a "minimum viable net (MVN)".

The learning network 623 is a MVN because if additional connections or nodes are attempted to be set to zero in learning network 623, image quality can suffer.

Once the MVN has been obtained with the learning network 623, "zero" regions (e.g., dark irregular regions in a graph) are mapped to the input 610. Each dark zone is likely to map to one or a set of parameters in the input space. For example, one of the zero regions may be linked to the number of views and number of channels in the raw data. Since redundancy in the network 623 corresponding to these parameters can be reduced, there is a highly likelihood that the input data can be reduced and generate equally good output. To reduce input data, new sets of raw data that correspond to the reduced parameters are obtained and run through the learning network 621. The network 620-623 may or may not be simplified, but one or more of the learning networks 620-623 is processed until a "minimum viable input (MVI)" of raw data input 610 is reached. At the MVI, a further reduction in the input raw data 610 may result in reduced image 630 quality. The MVI can result in reduced complexity in data acquisition, less demand on system components, reduced stress on patients (e.g., less breath-hold or contrast), and/or reduced dose to patients, for example.

By forcing some of the connections and nodes in the learning networks 620-623 to zero, the network 620-623 to build "collaterals" to compensate. In the process, insight into the topology of the learning network 620-623 is obtained. Note that network 621 and network 622, for example, have different topology since some nodes and/or connections have been forced to zero. This process of effectively removing connections and nodes from the network extends beyond "deep learning" and can be referred to as "deep-deep learning", for example.

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 7:
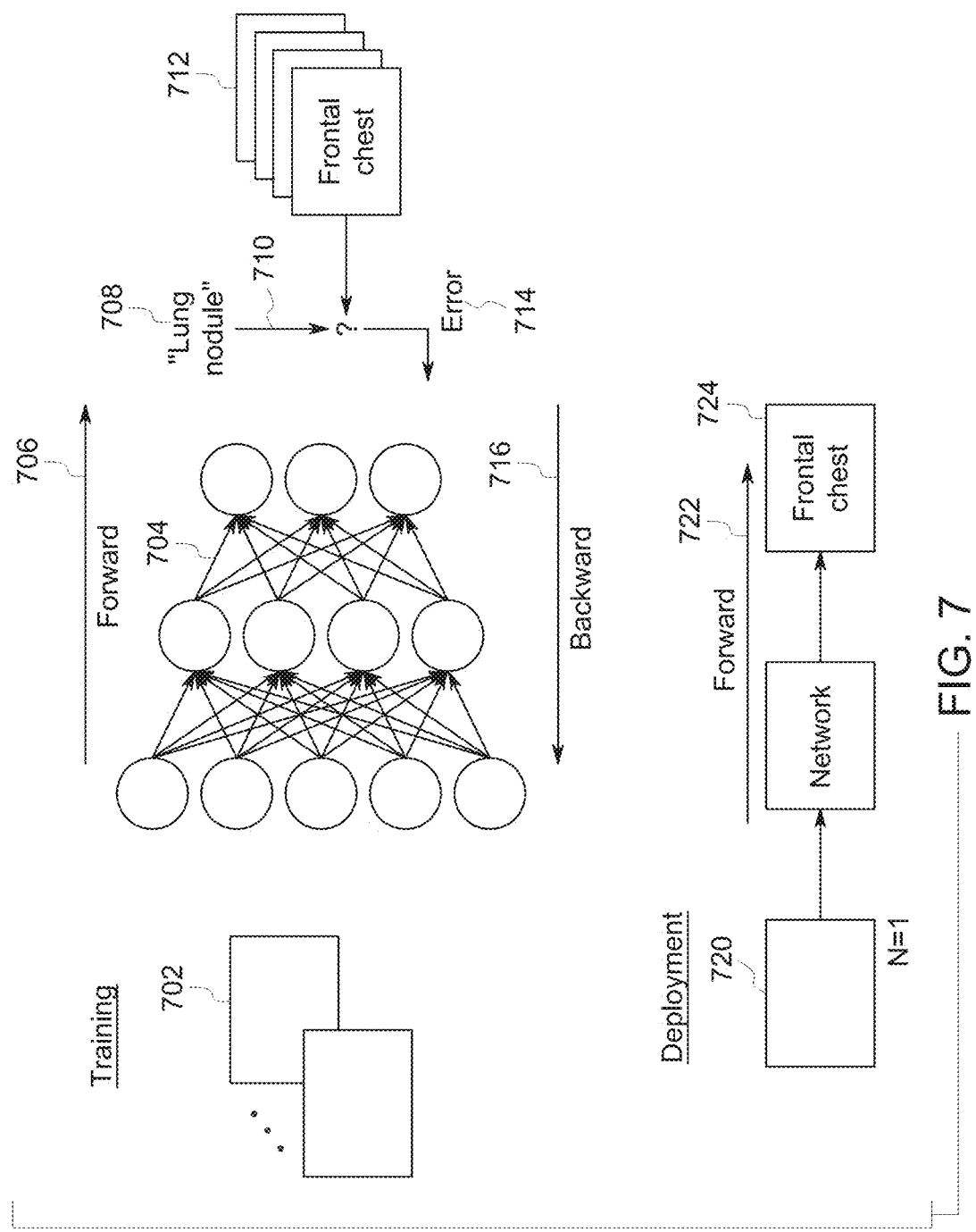
FIG. 7 is a schematic diagram of an embodiment for training and deployment phases of a learning network.

FIG. 7 illustrates example training and deployment phases of a learning network, such as a deep learning or other machine learning network. As shown in the example of FIG. 7, in the training phase, a set of inputs 702 is provided to a network 704 for processing. In this example, the set of inputs 702 can include facial features of an image to be identified. The network 704 processes the input 702 in a forward direction 706 to associate data elements and identify patterns. The network 704 determines that the input 702 represents a lung nodule 708. In training, the network result 708 is compared 710 to a known outcome 712. In this example, the known outcome 712 is a frontal chest (e.g., the input data set 702 represents a frontal chest identification, not a lung nodule). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Figure 8:
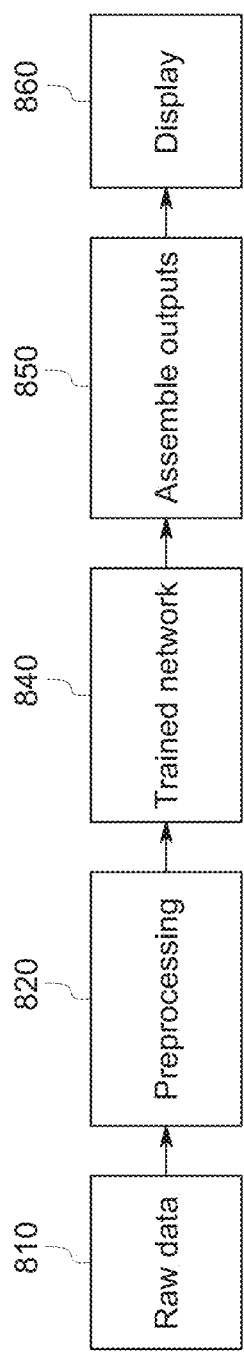
FIG. 8 is a schematic diagram of an embodiment of a product leveraging a trained network package to provide a deep learning product offering.

Once the comparison of network output 708 to known output 712 matches 710 according to a certain criterion or threshold (e.g., matches n times, matches greater than x percent, etc.), the training network 704 can be used to generate a network for deployment with an external system. Once deployed, a single input 720 is provided to a deployed learning network 722 to generate an output 724. In this case, based on the training network 704, the deployed network 722 determines that the input 720 is an image of a frontal chest 724. This same approach may be utilized in determining a tube or line, a reference or anatomical landmark, and/or the proper placement of the tube or line FIG. 8 illustrates an example product leveraging a trained network package to provide a deep and/or other machine learning product offering. As shown in the example of FIG. 8, an input 810 (e.g., raw data) is provided for preprocessing 820. For example, the raw input data 810 is preprocessed 820 to check format, completeness, etc. Once the data 810 has been preprocessed 820, it is fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device, etc.), etc.).

Figure 9A:
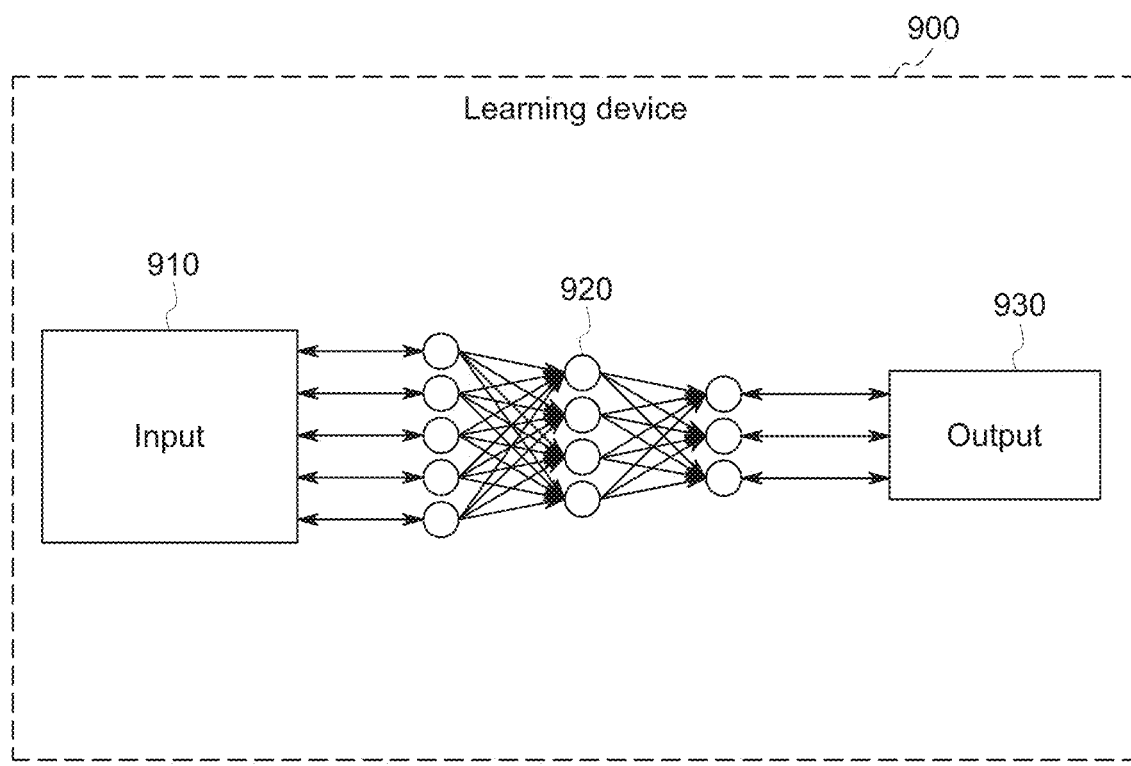
FIGS. 9A-9C is a schematic diagram of embodiments of various deep learning device configurations.
Figure 9B:
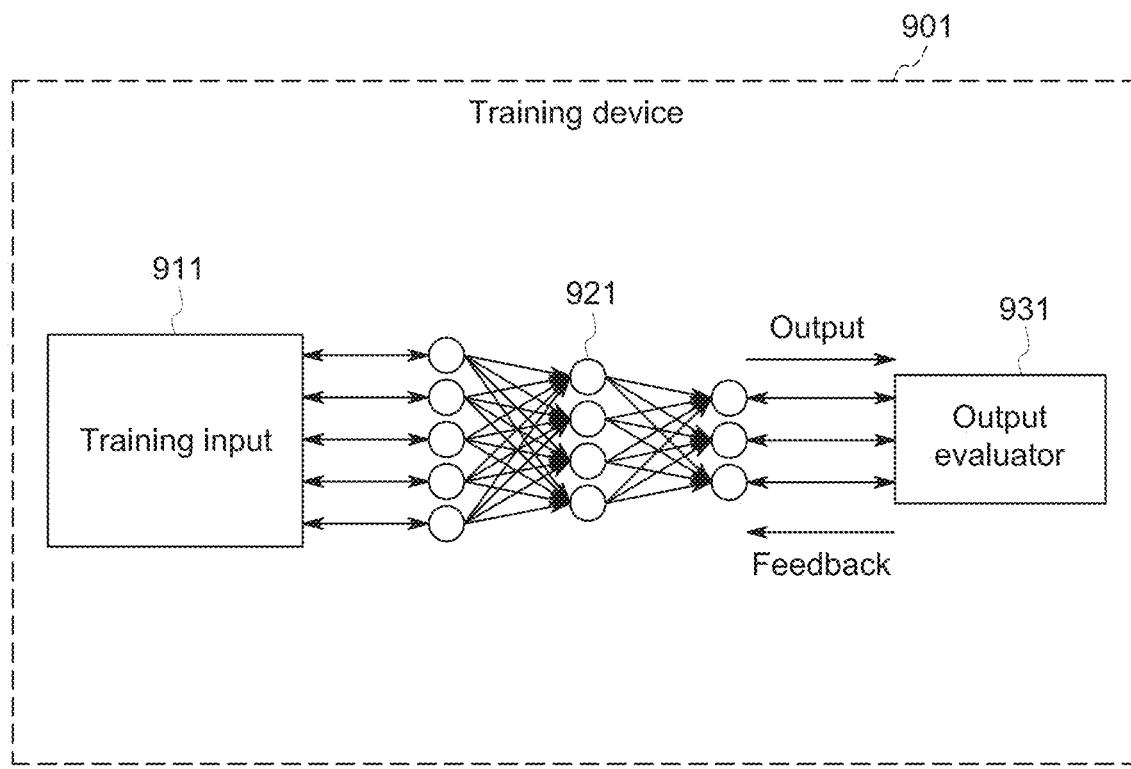
Figure 9C:
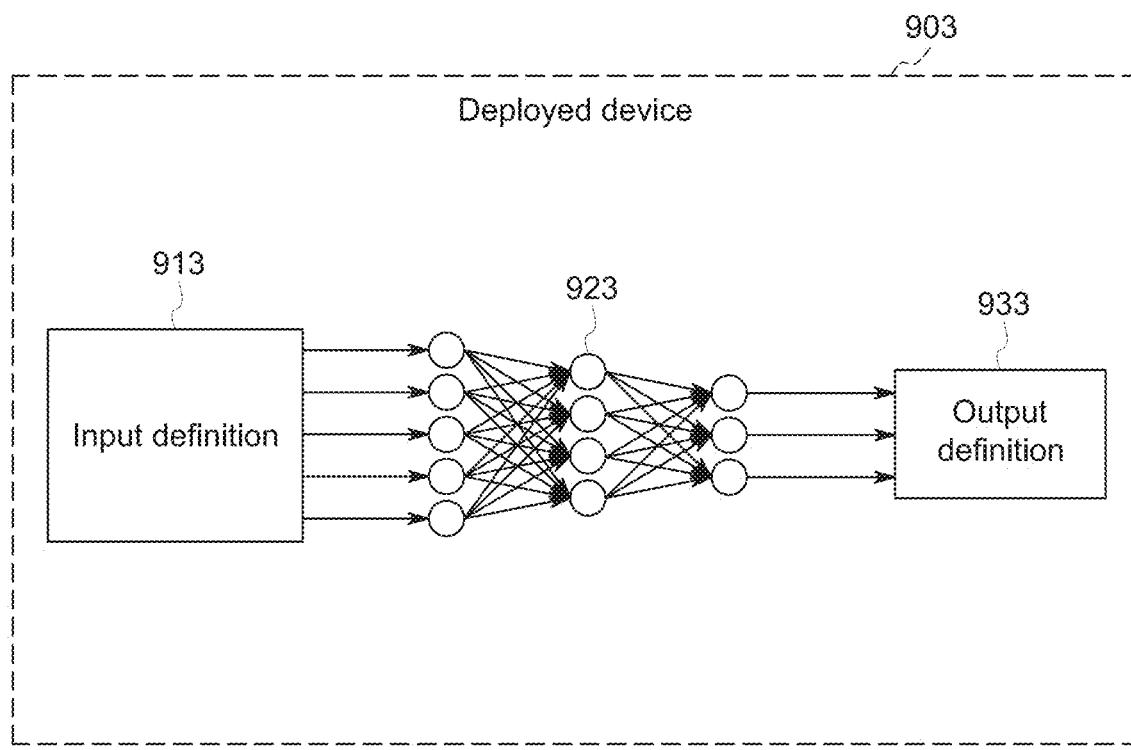

As discussed above, learning networks can be packaged as devices for training, deployment, and application to a variety of systems. FIGS. 9A-9C illustrate various learning device configurations. For example, FIG. 9A shows a general learning device 900. The example device 900 includes an input definition 910, a learning network model 920, and an output definition 930. The input definition 910 can include one or more inputs translating into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 can be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 can be deployed for use. While the training device 901 processes multiple inputs to learn, the deployed device 903 processes a single input to determine an output, for example. As shown in the example of FIG. 9C, the deployed device 903 includes an input definition 913, a trained network 923, and an output definition 933. The trained network 923 can be generated from the network 921 once the network 921 has been sufficiently trained, for example. The deployed device 903 receives a system input 913 and processes the input 913 via the network 923 to generate an output 933, which can then be used by a system with which the deployed device 903 has been associated, for example.

In certain examples, condition identification (e.g., placement of a tube or line) and progression can be determined through AI-driven analysis of associated image data for a patient.

Figure 10:
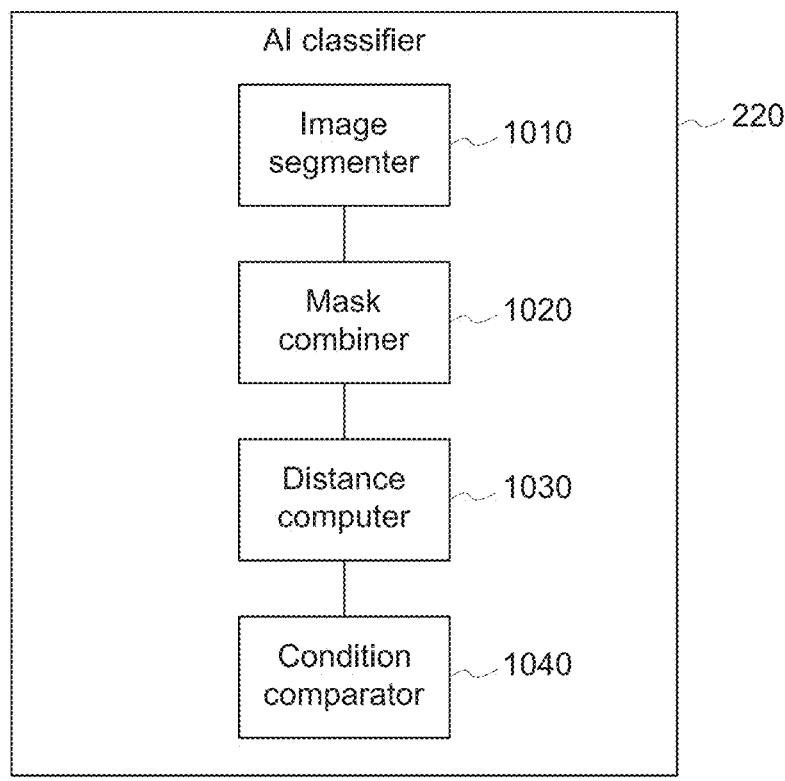
FIG. 10 is a schematic diagram of an embodiment of an implementation of the artificial intelligence classifier of FIG. 2 to process image data to be used by an artificial intelligence model to quantify a condition.

FIG. 10 illustrates an example implementation of the AI classifier 220 to process image data to be used by an AI model to quantify a condition (e.g., placement of a tube or line). The example implementation of the classifier 220 enables annotation of one or more images including an organ region and a region of interest within the organ region. The example classifier 220 of FIG. 10 includes an image segmenter 1010, a mask combiner 1020, and a condition comparator 1040.

The example image segmenter 1010 is to identify a first mask and a second mask in an input image. For example, the image segmenter 1010 processes the image to segment a region of interest within an organ region identified in the image to obtain a first mask. The first mask is a segmentation mask is a filter that includes the region of interest in the image and excludes the remainder of the image. The mask can be applied to image data to exclude all but the region of interest, for example. The mask can be obtained using a convolutional neural network model, for example, such as the network 400, 500 shown in FIGS. 4-5, a generative adversarial network, etc. The image segmenter 1010 further processes the image to segment the organ region according to one or more criterion to obtain a second mask. For example, the second mask can represent the organ region, an area of the organ region outside the region of interest, etc.

For example, if the organ region is a lung (and the surrounding area such as the trachea), and the region of interest is a tube or line identified in the trachea, the first mask is generated to identify the medically placed tube or line, and the second mask is generated to identify the entire organ region. In another embodiment, if the organ region is a stomach, and the region of interest is a tube or line identified in the in the stomach, the first mask is generated to identify the medically placed tube or line, and the second mask is generated to identify the entire organ region. In a further embodiment, if the organ region is a heart (and the surrounding area such as veins or other vasculature), and the region of interest is a tube or line identified in a vein or other vasculature near the heart, the first mask is generated to identify the medically placed tube or line, and the second mask is generated to identify the entire organ region. Thus, in regards to a medically placed tube or line, a first mask is generated for the tube or line and a second mask is generated for the entire organ region where the tube or line is placed (e.g., vasculature system, heart, lung, stomach, trachea, chest, pleural space, etc.).

The example combiner 1020 combines the first mask and the second mask and associated areas with annotation terms in the image. Annotations can be relative qualification terms to produce quantification, for example. For example, mask areas can be combined with descriptive terms such as foggy, patchy, dense, etc., to compute relative density values for the region of interest and organ region in the image. Image areas (e.g., areas of frontal and lateral images, etc.) can be combined to produce a volume metric, for example.

The example distance computer 1030 determines a distance between an end of an identified tube or line and a reference or anatomical landmark (or determines a position of the tube or line relative to the landmark). The example condition comparator 1040 compares the distance or measured positions to a preset distance or desired position for the type of tube or line and/or region of interest where the tube or line is placed (e.g., in accordance with predetermined rules). Based on this comparison, the condition comparator 1040 can determine whether the end of the tube or line is properly placed relative to the reference or anatomical landmark.

Thus, the AI classifier 220 can be configured to annotate a medical image or set of related medical image(s) for AI/machine learning/deep learning/CAD algorithm training, to quantify conditions. Such methods are consistent, repeatable methodologies which could replace common subjective methods of today, enabling automatic, accurate detection of the presence of a medically placed tube or line and its placement.

While example implementations are illustrated in conjunction with FIGS. 1-10, elements, processes and/or devices illustrated in conjunction with FIGS. 1-10 can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 11:
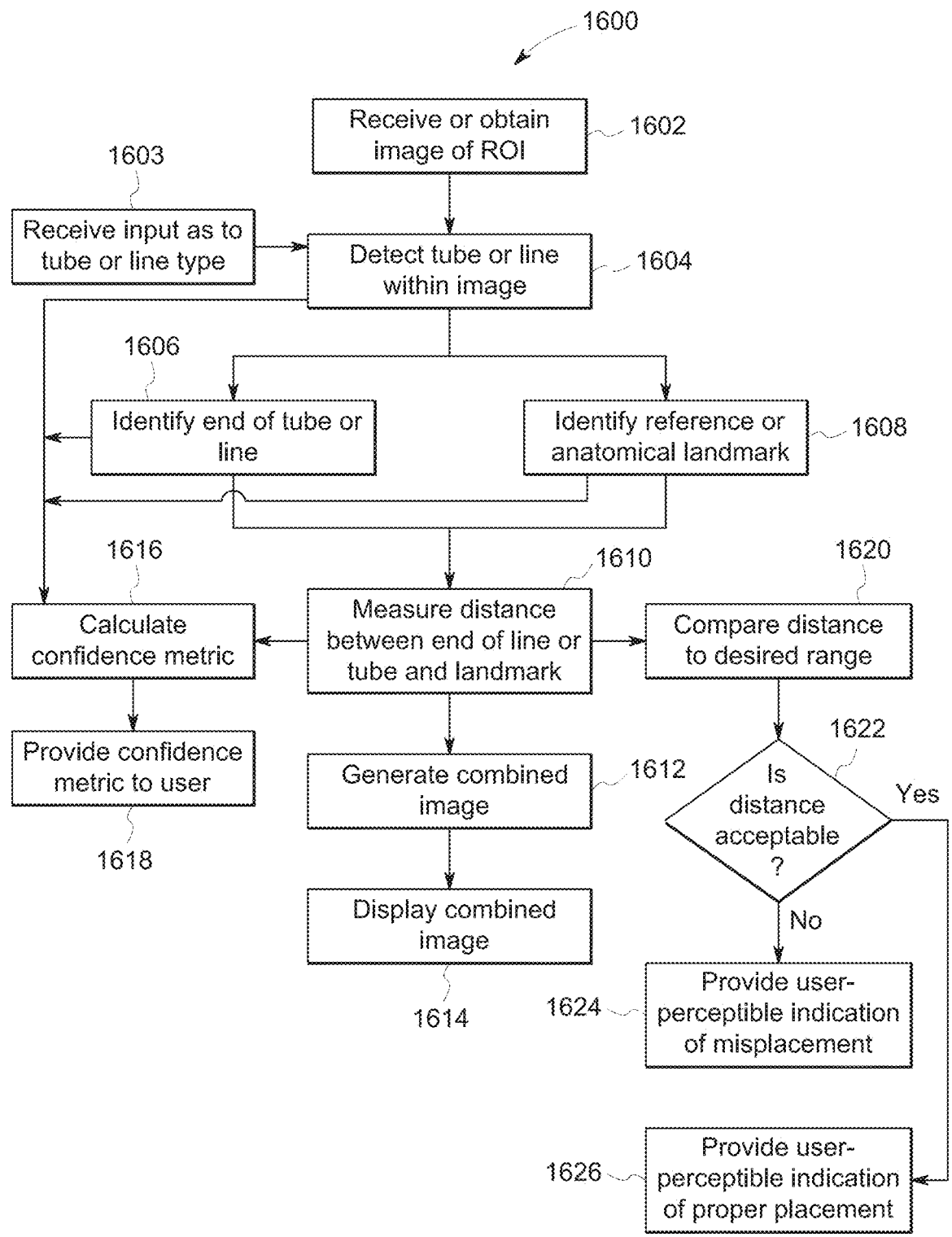
FIG. 11 is a flow diagram of an embodiment of a method for determining a placement of a medically placed tube or line within a region of interest.

A flowchart representative of example machine readable instructions for implementing components disclosed and described herein are shown in conjunction with at least FIG. 11. In the examples, the machine readable instructions include a program for execution by a processor such as the processor 1312 shown in the example processor platform 1300 discussed below in connection with FIG. 14. The program may be embodied in machine readable instructions stored on a tangible computer readable storage medium such as a CD-ROM, a floppy disk, a hard drive, a digital versatile disk (DVD), a Blu-ray disk, or a memory associated with the processor 1312, but the entire program and/or parts thereof could alternatively be executed by a device other than the processor 1312 and/or embodied in firmware or dedicated hardware. Further, although the example program is described with reference to the flowchart illustrated in conjunction with at least FIG. 11, many other methods of implementing the components disclosed and described herein may alternatively be used. For example, the order of execution of the blocks may be changed, and/or some of the blocks described may be changed, eliminated, or combined. Although the flowchart of at least FIG. 11 depicts an example operation in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIG. 11 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIG. 11 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As mentioned above, these techniques may be utilized to identify a medically placed tube or line and to determine if medically placed tube or line is properly placed. For example, the medically placed tube or line may be an endotracheal tube and the proper placement of the endotracheal tube within the trachea (e.g., relative to the canna) may be determined. In another example, the medically placed tube or line may be a nasogastric tube and the proper placement of the nasogastric tube within the stomach may be determined. In a further example, the medically placed tube or line may be a vascular line (e.g., PICC line, centrally inserted central catheter line, etc.) and the proper placement of the vascular line within a certain vasculature may be determined. In yet a further example, the medically placed tube line may be a chest tube and the proper placement of the chest tube within the chest (in particular, the plenum space) may be determined. These examples are intended to be non-limiting, and any other tube or line inserted within a region of interest of body may be identified and it proper placement determined.

FIG. 11 is a flow diagram of an embodiment of a method 1600 for determining a placement of a medically placed tube or line within a region of interest. One or more steps of the method may be performed by the processor platform 1600 in FIG. 13. One or more steps may be performed simultaneously or in a different order from that illustrated in FIG. 11. The method 1600 includes receiving or obtaining an image (e.g., chest image) of a patient that includes a region of interest (ROI) (block 1602). The image may include a medically placed tube or line inserted within the region of interest. The image may be provided while the patient has the tube or line inserted. The method 1600 also includes receiving or obtaining an input regarding the type of tube or line to be detected (e.g., endotracheal tube) and/or the region of interest for tube or line to be inserted within (e.g., trachea) (block 1603). The input may be a user defined distance or rules for defining the proper placement of the end of the medically placed tube or line relative to a reference or anatomical location. In certain embodiments, the input may simply be the type of tube or line and/or the desired region of interest for the tube or line to be properly placed within. Based on this input, certain defined distances or rules (e.g., left, right, above, and/or below a specific anatomical location) may be utilized that define a proper placement of the end of the specific tube or line within a specific region of interest (e.g., a specific distance range above the carina for an endotracheal tube). The method 1600 also includes detecting the tube or line within the image (block 1604) utilizing the techniques described above. The method 1600 includes identifying an end (e.g., distal end) of the tube or line within the region of interest in the image (block 1606). The method 1600 also includes identifying a reference or anatomical landmark within the image (block 1608). The reference or anatomical landmark will vary based on the type of tube or line utilized and the region of interest that the tube or line is disposed within. For example, for an endotracheal tube, the reference or anatomical landmark may be the carina of the trachea. For a nasogastric tube, the reference or anatomical landmark may be a location within the stomach below the gastroesophageal junction. For a vascular line, the reference or anatomical landmark may be a location within the superior vena cava, the inferior vena cava, or proximal right atrium.

Upon identifying the end of the tube or line and the reference or anatomical landmark, the method 1600 includes measuring a distance between the end of the tube or line and the reference or anatomical landmark (block 1610). The method 1600 includes generating a combined image with indications of the end of the tube or line, the reference or anatomical landmark, and/or the measured distance (block 1612). Generating the combined image includes superimposing various markers on the received image of the patient. For example, a color coding (e.g., color coded graphical overlay) may be superimposed on the detected tube or line. In certain embodiments, the patient may include more than one tube or line and the tube or line of interest is color coded. A graphical marker may be superimposed on the image to indicate the end of the line or tube. Another graphical marker may be superimposed on the image to indicate the reference or anatomical landmark. The graphical markers may include the same shape or different shapes. Non-limiting examples of the shapes may be an open circle or other elliptical shape, open rectilinear shape, open triangular shape, or another shape. The different graphical and the tube may be color coded with different colors. For example, the graphical marker for the tube or line, the graphical marker for the reference or anatomical landmark, and the tube or line may be green, blue, and yellow, respectively. A graphical marker may also be superimposed on the image indicating a distance between the end of the tube or line and the reference or anatomical landmark when a distance is calculated. The graphical marker for the distance may also include the measurement value. The method 1600 further includes displaying the combined image on a display (block 1614). The combined image may be displayed in real-time to the medical personnel enabling them to adjust the placement of the tube or line if need be. In certain embodiments, the combined image may be displayed as a DICOM image.

In certain embodiments, the method 1600 includes calculating one or more respective confidence metrics (block 1616). The confidence metrics may be for the calculated distance, for the determination of the presence of the medically placed tube or line, for an accuracy in detecting the end of the tube or line, and/or for an accuracy in detecting the reference or anatomical landmark. The confidence metric may include a confidence level or confidence interval. The confidence metric may be stored for future reference. In certain embodiments, the method 1600 may include providing one or more of the confidence metrics to a user (block 1618). For example, the confidence metrics may be displayed on the combined image or provided on a separate device (e.g., user's device). In certain embodiments, the confidence metrics may be written into a standard or private information tag (e.g., DICOM) and made visible in subsequent information systems that the image is sent too (e.g., PACS).

In certain embodiments, in determining whether the end of the medically placed tube or line is placed properly (e.g., via the deep learning networks models), the method 1600 includes comparing the measured distance between the end of the tube or line and the reference or anatomical landmark to a desired threshold (block 1620) and determining if the distance is acceptable (block 1622). The desired threshold may represent an acceptable range for the distance between the end of the tube or line and the reference or anatomical landmark for the tube or line to be correctly placed. For example, for an endotracheal tube, the desired threshold may be 2 to 3 centimeters (cm) above the carina (e.g., anatomical landmark). For a nasogastric tube, the desired threshold may be a range of distance below the gastroesophageal junction. If the measured distance is not acceptable, the method 1600 includes providing a user-perceptible indication of misplacement (block 1624). The indication may be provided on the display where the combined image is displayed or provided on another device (e.g., the user's device). The indication may be text stating that the tube or line is misplaced. In certain embodiments, the text may be more specific and state the tube or line is too high (e.g., greater than the desired 2 to 3 cm for the endotracheal tube placement) or too low (e.g., less than the 2 cm for the endotracheal tube placement). In certain embodiments, the text may provide further instructions (e.g., to raise or lower the end of the tube or line a certain distance). In some embodiments, the text may be color coded (e.g., in orange or red) to further indicate the misplacement. In some embodiments, the indication may be provided via color coding of one or more graphical markers or the tube or line displayed on the combined image. For the example, one or more of the graphical markers (e.g., for the end of tube or line, for the reference or anatomical landmark, and/or the indication of the measured distance there between) and/or the tube or line may be color coded a specific color (e.g., red or orange) to indicate the misplacement. Alternatively or in addition, one or more of the graphical markers may flash if the tube or line is misplaced. If the measured distance is acceptable, the method 1600 includes providing a user-perceptible indication of proper placement of the tube or line (block 1626). The indication may be provided on the display where the combined image is displayed or provided on another device (e.g., the user's device). The indication for proper placement may be text stating the tube or line is properly placed. In certain embodiments, the indication for proper placement may be provided via color coding one or more graphical markers of the tube or line displayed on the combined image (e.g., all the graphical markers and/or the tube or line may be color coded green). In certain embodiments, the indication of proper placement or misplacement may be written into a standard or private information tag (e.g., DICOM) and made visible in subsequent information systems that the image is sent too (e.g., PACS). In certain embodiments, the determination as to whether the end of the medically placed tube or line may be manually done by the medical personnel viewing the displayed combined image.

Figure 12:
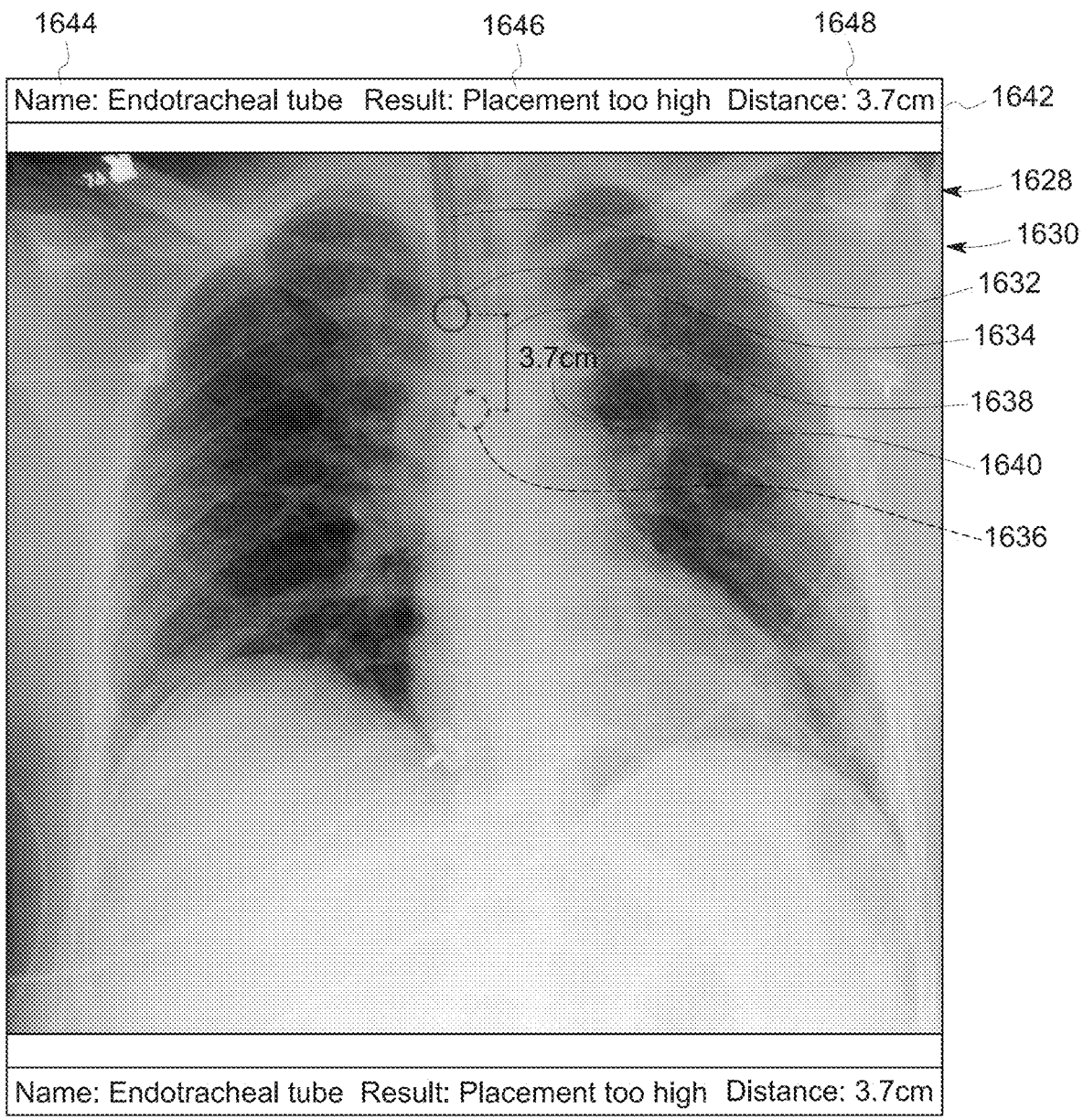
FIG. 12 is an example of a combined image identifying a tube or line within a patient.

FIG. 12 is an example of a combined image 1628 (e.g., DICOM image) identifying a tube or line within a patient that may be displayed on a display. As depicted, the combined image 1628 is a chest image 1630 of a patient showing an endotracheal tube 1632 disposed within the trachea. A graphical marker 1634 (e.g., circle) overlaid on the chest image 1630 indicates the location of the end of the endotracheal tube 1632. A graphical marker 1636 (e.g., dashed circle) overlaid on the chest image indicates a reference or anatomical location (e.g., carina). A graphical marker 1638 indicates a distance (e.g., vertical distance) between the end of the endotracheal tube 1632 and the reference or anatomical location 1636. A numerical value 1640 for the measured distance accompanies the graphical marker 1638. In certain embodiments, a confidence metric in the measured distance generated by the artificial intelligence is also displayed (e.g., as depicted a confidence level). In certain embodiments, the tube 1632, the graphical marker 1634, and/or the graphical marker 1636 may be color coded (e.g., yellow, green, and red). The combined image 1628 includes a header 1642 that includes information related to the image 1628. For example, as depicted, the header 1642 includes the type of tube or line 1644 (e.g., endotracheal tube), whether the placement of the tube is proper or not 1646, and the calculated distance 1648 between the end of the tube and the reference or anatomical marker. In certain embodiments, the header 1642 may include an indication as to whether the tube or line was detected. In certain embodiments, one or more confidence metrics may be displayed on the image 128 (e.g., for the calculated distance, for the determination of the presence of the medically placed tube or line, for an accuracy in detecting the end of the tube or line, and/or for an accuracy in detecting the reference or anatomical landmark).

Figure 13:
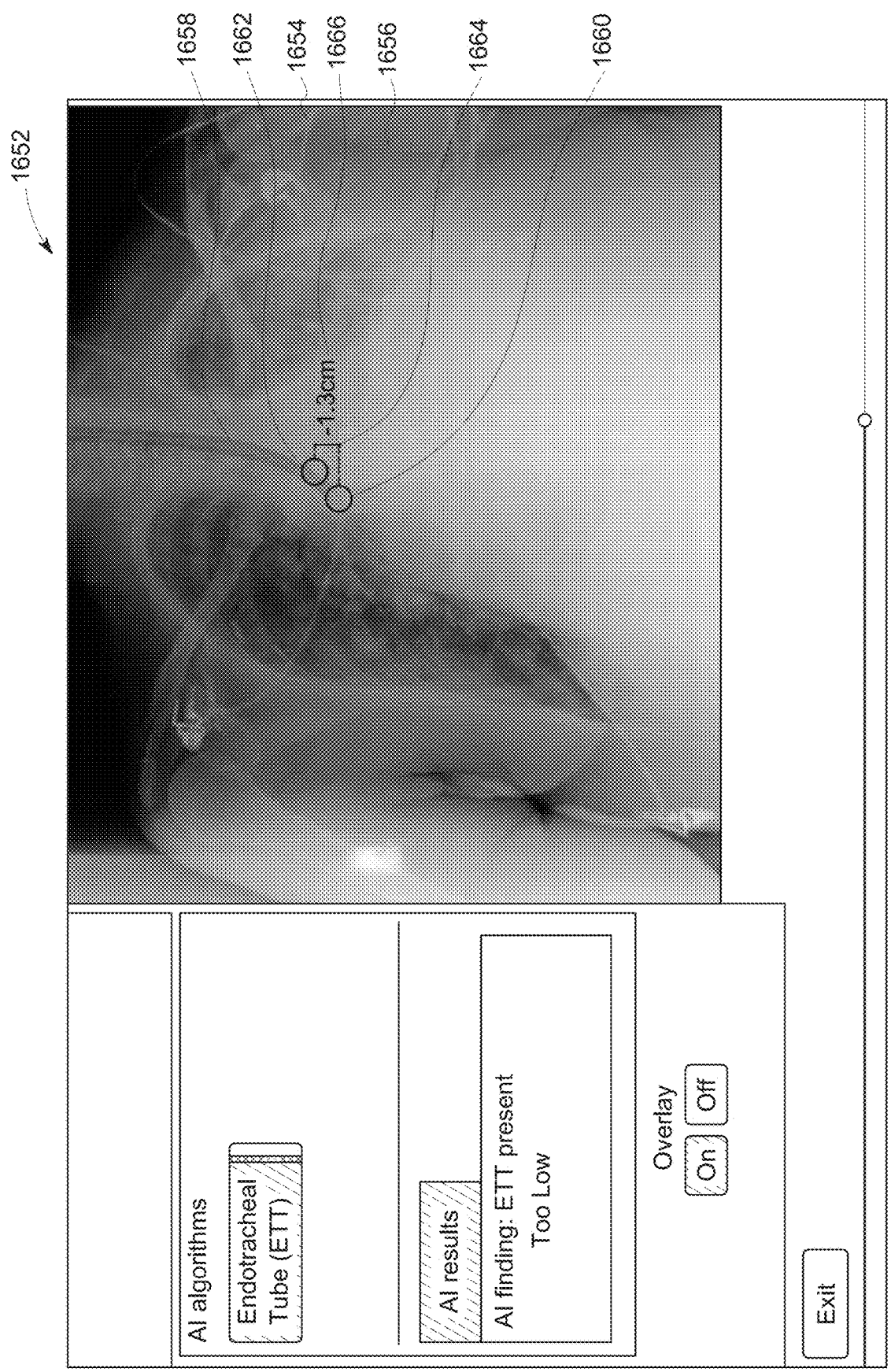
FIG. 13 is a schematic diagram of a user interface having a combined image identifying a tube or line within a patient.

FIG. 13 is a schematic diagram of a user interface 1652 having a combined image 1654 identifying a tube or line within a patient that may be displayed on a display. As depicted, the combined image 1652 is a chest image 1656 of a patient showing an endotracheal tube 1658 disposed within the trachea. A graphical marker 1660 (e.g., circle) overlaid on the chest image 1656 indicates the location of the end of the endotracheal tube 1658. A graphical marker 1662 (e.g., circle) overlaid on the chest image 1656 indicates a reference or anatomical location (e.g., carina). A graphical marker 1664 indicates a distance (e.g., vertical distance) between the end of the endotracheal tube 1660 and the reference or anatomical location 1662. A numerical value 1666 for the measured distance accompanies the graphical marker 1664. As mentioned above, in certain embodiments, the tube 1658, the graphical marker 1660 and/or the graphical marker 1662 may be color coded (e.g., yellow, green, and red). The user interface 1652 includes an indication 1668 of an analysis by the AI of the placement of the end of the tube or line (e.g., indicated by marker 1660) relative to the reference or anatomical location (e.g., indicated by marker 1662). As depicted, the indication 1668 indicates that the end of the tube or line is too low relative to the reference or anatomical location. In certain embodiments, the indication may state the tube or line is placed properly, misplaced, provide an indication of what is wrong with the location, or provide instructions for correcting a location.

Figure 14:
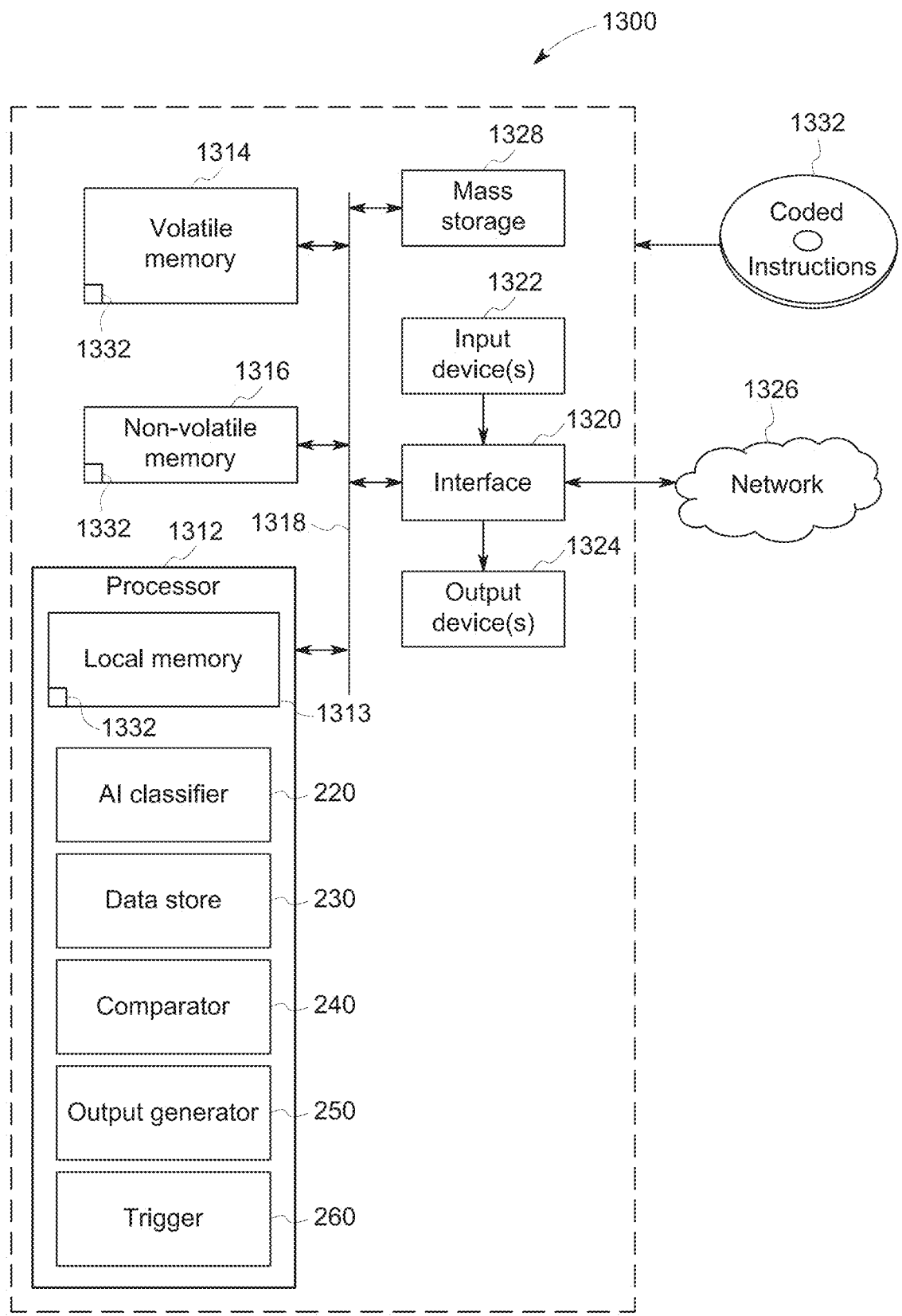
FIG. 14 is a schematic diagram of an embodiment of a processor platform structured to execute the example machine readable instructions to implement components disclosed and described herein.

FIG. 14 is a block diagram of an example processor platform 1300 structured to executing the instructions of at least FIG. 11 to implement the example components disclosed and described herein. The processor platform 1300 can be, for example, a server, a personal computer, a mobile device (e.g., a cell phone, a smart phone, a tablet such as an iPad™), a personal digital assistant (PDA), an Internet appliance, or any other type of computing device.

The processor platform 1300 of the illustrated example includes a processor 1312. The processor 1312 of the illustrated example is hardware. For example, the processor 1312 can be implemented by integrated circuits, logic circuits, microprocessors or controllers from any desired family or manufacturer.

The processor 1312 of the illustrated example includes a local memory 1313 (e.g., a cache). The example processor 1312 of FIG. 14 executes the instructions of at least FIG. 11 to implement the systems, infrastructure, displays, and associated methods of FIGS. 1-13 such as the example data source 210, AI classifier 220, data store 230, comparator 240, output generator 250, trigger 260, etc. The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a clock controller.

The processor platform 1300 of the illustrated example also includes an interface circuit 1320. The interface circuit 1320 may be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 1312. The input device(s) can be implemented by, for example, a sensor, a microphone, a camera (still or video, RGB or depth, etc.), a keyboard, a button, a mouse, a touchscreen, a track-pad, a trackball, isopoint and/or a voice recognition system.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1320 of the illustrated example, thus, typically includes a graphics driver card, a graphics driver chip or a graphics driver processor.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

The coded instructions 1332 of FIG. 14 may be stored in the mass storage device 1328, in the volatile memory 1314, in the non-volatile memory 1316, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Thus, certain examples facilitate image acquisition and analysis at the point of care such as via a portable imaging device at the point of patient imaging. If images should be re-taken, further analysis done right away, and/or other criticality explored sooner, rather than later, the example systems, apparatus, and methods disclosed and described herein can facilitate such action to automate analysis, streamline workflow, and improve patient care.

Certain examples provide a specially-configured imaging apparatus that can acquire images and operate as a decision support tool at the point of care for a critical care team. Certain examples provide an imaging apparatus that functions as a medical device to provide and/or facilitate diagnosis at the point of care to detect radiological findings, etc. The apparatus can trigger a critical alert for a radiologist and/or critical care team to bring immediate attention to the patient. The apparatus enables patient triaging after the patient's exam, such as in a screening environment, wherein negative tests allow the patient to return home, while a positive test would require the patient to be seen by a physician before returning home.

In certain examples, a mobile device and/or cloud product enables a vendor-neutral solution, proving point of care alerts on any digital x-ray system (e.g., fully integrated, upgrade kit, etc.). In certain examples, embedded AI algorithms executing on a mobile imaging system, such as a mobile x-ray machine, etc., provide point of care alerts during and/or in real-time following image acquisition, etc.

By hosting AI on the imaging device, the mobile x-ray system can be used in rural regions without hospital information technology networks, or even on a mobile truck that brings imaging to patient communities, for example. Additionally, if there is long latency to send an image to a server or cloud, AI on the imaging device can instead be executed and generate output back to the imaging device for further action. Rather than having the x-ray technologist moved onto the next patient and the x-ray device no longer at the patient's bedside with the clinical care team, image processing, analysis, and output can occur in real time (or substantially real time given some data transfer/retrieval, processing, and output latency) to provide a relevant notification to the clinical care team while they and the equipment are still with or near the patient. For trauma cases, for example, treatment decisions need to be made fast, and certain examples alleviate the delay found with other clinical decision support tools.

Mobile X-ray systems travel throughout the hospital to the patient bedside (e.g., emergency room, operating room, intensive care unit, etc. Within a hospital, network communication may be unreliable in "dead" zones of the hospital (e.g., basement, rooms with electrical signal interference or blockage, etc.). If the X-ray device relies on building Wi-Fi, for example, to push the image to a server or cloud which is hosting the AI model and then wait to receive the AI output back to the X-ray device, then patient is at risk of not having reliability in critical alerts when needed. Further, if a network or power outage impacts communications, the AI operating on the imaging device can continue to function as a self-contained, mobile processing unit.

Examples of alerts generated for general radiology can include critical alerts (e.g., for mobile x-ray, etc.) such as tubes and line placement, pleural effusion, lobar collapse, pneumoperitoneum, pneumonia, etc.; screening alerts (e.g., for fixed x-ray, etc.) such as tuberculosis, lung nodules, etc.; quality alerts (e.g., for mobile and/or fixed x-ray, etc.) such as patient positioning, clipped anatomy, inadequate technique, image artifacts, etc.

Thus, certain examples improve accuracy of an artificial intelligence algorithm. Certain examples factor in patient medical information as well as image data to more accurately predict presence of a critical finding, an urgent finding, and/or other issue.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

Technical effects of the disclosed subject matter include providing systems and methods that utilize AI (e.g., deep learning networks) to determine whether or not a medically placed tube or line is properly placed within a region of interest (e.g., relative to a reference or anatomical landmark). The systems and methods may provide feedback in real time that in a more accurate and quicker manner determine if a medically placed tube or line is misplaced. Thus, enabling fast intervention, if needed, to move the tube or line to the appropriate location for patient safety.

This written description uses examples to disclose the subject matter, including the best mode, and also to enable any person skilled in the art to practice the subject matter, including making and using any devices or systems and performing any incorporated methods. The patentable scope of the disclosed subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical image processing system, comprising:
   a display;
   a processor; and
   a memory storing processor-executable code that when executed by the processor causes:
      receiving an image of a region of interest of a patient with a medical tube or line disposed within the region of interest;
      detecting the medical tube or line within the image;
      detecting a reference landmark within the region of interest within the image, wherein the reference landmark is internal to the patient;
      generating a combined image by superimposing a first graphical marker on the image that indicates an end of the medical tube or line and a second graphical marker on the image that indicates the reference landmark; and
      displaying the combined image on the display.

2. The medical image processing system of claim 1, wherein the processor-executable code when executed by the processor causes calculating a measured position of the end of the medical tube or line relative to the reference landmark, and wherein generating the combined image comprises superimposing a third graphical marker on the image that indicates the measured position.

3. The medical image processing system of claim 1, wherein the processor-executable code when executed by the processor causes calculating respective confidence scores for one or more of a calculated distance between the end of the medical tube or line and the reference landmark, a determination as to whether a medical tube or line is present within the image, an accuracy of a detection of the end of the medical tube or line, or an accuracy of a detection of the reference landmark.

4. The medical image processing system of claim 1, wherein the processor-executable code when executed by the processor causes determining whether the medical tube or line is properly placed relative to the reference landmark.

5. The medical image processing system of claim 4, wherein the processor-executable code when executed by the processor causes providing a user-perceptible indication to a user when the medical tube or line is misplaced relative to the reference landmark.

6. The medical image processing system of claim 1, wherein the medical tube or line comprises a chest tube, a nasogastric tube, endotracheal tube, vascular line, a peripherally inserted central catheter, or a catheter.

7. The medical image processing system of claim 1, wherein the reference landmark comprises a carina, a chest cavity, a segmented lung, a diaphragm, or a stomach.

8. The medical image processing system of claim 1, wherein detecting the medical tube or line within the image comprises utilizing one or more deep learning network models to detect the medical tube or line within the image.

9. The medical image processing system of claim 1, wherein generating the combined image comprises superimposing on the image a colored graphical overlay over the medical tube or line to indicate the medical tube or line.

10. A method for medical image processing, comprising:
receiving, via a processor, an image of a region of interest of a patient with a medical tube or line disposed within the region of interest;
detecting, via the processor, the medical tube or line within the image;
detecting, via the processor, a reference landmark within the region of interest within the image, wherein the reference landmark is internal to the patient;
generating, via the processor, a combined image by superimposing a first graphical marker on the image that indicates an end of the medical tube or line and a second graphical marker on the image that indicates the reference landmark; and
causing, via the processor, display of the combined image on a display.

11. The method of claim 10, comprises calculating, via the processor, a measured position of the end of the medical tube or line relative the reference landmark, and wherein generating the combined image comprises superimposing, via the processor, a third graphical marker on the image that indicates the measured position.

12. The method of claim 10, comprises calculating, via the processor, respective confidence scores for one or more of a calculated distance between the end of the medical tube or line and the reference landmark, a determination as to whether a medical tube or line is present within the image, an accuracy of a detection of the end of the medical tube or line, or an accuracy of a detection of the reference landmark.

13. The method of claim 10, comprising determining, via the processor, whether the medical tube or line is properly placed relative to the reference landmark.

14. The method of claim 13, comprising providing, via the processor, a user-perceptible indication to a user when the medical tube or line is misplaced relative to the reference landmark.

15. The method of claim 10, wherein detecting the medical tube or line within the image comprises utilizing, via the processor, one or more deep learning network models to detect the medical tube or line within the image.

16. A non-transitory, computer-readable medium, the computer-readable medium comprising processor-executable code configured to:
receive an image of a region of interest of a patient with a medical tube or line disposed within the region of interest;
detect the medical tube or line within the image and a reference landmark within the region of interest within the image, wherein the reference landmark is internal to the patient;
generate a combined image by superimposing a first graphical marker on the image that indicates an end of the medical tube or line and a second graphical marker on the image that indicates the reference landmark; and
display the combined image on a display.

* * * * *